(12) United States Patent
Adaway

(10) Patent No.: US 9,227,936 B2
(45) Date of Patent: Jan. 5, 2016

(54) METHODS OF PRODUCING SULFILIMINE COMPOUNDS

(71) Applicant: DOW AGROSCIENCES LLC, Indianapolis, IN (US)

(72) Inventor: Timothy J. Adaway, Midland, MI (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 13/768,543

(22) Filed: Feb. 15, 2013

(65) Prior Publication Data

US 2013/0217883 A1 Aug. 22, 2013

Related U.S. Application Data

(60) Provisional application No. 61/599,489, filed on Feb. 16, 2012.

(51) Int. Cl.
| | |
|---|---|
| *C07D 211/70* | (2006.01) |
| *C07D 211/82* | (2006.01) |
| *C07D 213/57* | (2006.01) |
| *C07D 213/56* | (2006.01) |
| *C07D 213/34* | (2006.01) |

(52) U.S. Cl.
CPC .................................. *C07D 213/34* (2013.01)

(58) Field of Classification Search
None
See application file for complete search history.

(56) References Cited

U.S. PATENT DOCUMENTS

| 2,573,733 | A | * | 11/1951 | Salvin et al. .................. 552/239 |
|---|---|---|---|---|
| 4,085,093 | A | | 4/1978 | Hopper et al. |
| 5,973,148 | A | | 10/1999 | Ringer et al. |
| 7,678,920 | B2 | * | 3/2010 | Zhu et al. ...................... 546/313 |
| 7,754,888 | B2 | | 7/2010 | Loso et al. |
| 7,868,027 | B2 | | 1/2011 | Podhorez et al. |
| 2005/0228027 | A1 | | 10/2005 | Zhu et al. |
| 2008/0207910 | A1 | | 8/2008 | Podhorez et al. |

FOREIGN PATENT DOCUMENTS

WO    WO 2008/106006 A1 *  9/2008

OTHER PUBLICATIONS

Weinbrenner, S. et al. Purification Principles in High-Speed Solution-Phase Synthesis. Combinatorial Chemistry. 2006, p. 2.*
International Search Report and Written Opinion for PCT Application No. PCT/US2013/026377, dated Jun. 28, 2013.

* cited by examiner

*Primary Examiner* — Janet L Andres
*Assistant Examiner* — Ben S Michelson
(74) *Attorney, Agent, or Firm* — Carl D. Corvin; Traskbritt, P.C.

(57) ABSTRACT

Methods of producing a sulfilimine compound, such as N-cyano-S-methyl-S-[1-(6-trifluoromethyl-3-pyridinyl)ethyl] sulfilimine or other substituted sulfilimine compound. The method includes combining a sulfide compound, cyanamide, a hypochlorite compound, and a base, and oxidizing the sulfide compound to form the sulfilimine compound. The sulfide compound may include a 2-trifluoromethyl-5-(1-substituted) alkyl-thiopyridine compound. The base may include sodium hydroxide. A buffer, such as a phosphate buffer, may, optionally, be used in the reaction.

13 Claims, No Drawings

METHODS OF PRODUCING SULFILIMINE COMPOUNDS

CROSS-REFERENCE TO RELATED APPLICATION

This application claims the benefit of U.S. Provisional Patent Application Ser. No. 61/599,489, filed Feb. 16, 2012, the disclosure of which is hereby incorporated herein in its entirety by this reference.

TECHNICAL FIELD

Embodiments of the present disclosure relate to methods of producing sulfilimine compounds, such as methods of producing sulfilimine compounds from sulfide compounds.

BACKGROUND

Substituted sulfilimine compounds are useful intermediates in the preparation of sulfoximine compounds, which have insecticidal activity. Cyano-substituted sulfilimine compounds have been prepared by reaction of a corresponding sulfide compound with cyanamide in the presence of iodobenzene diacetate. However, iodobenzene diacetate is expensive and causes waste disposal problems.

Substituted sulfilimine compounds have also been prepared by replacing the iodobenzene diacetate with hypochlorite. A corresponding sulfide compound is reacted with cyanamide in the presence of the hypochlorite. However, a corresponding sulfoxide compound is also produced as one of the reaction by-products. The yield of the substituted sulfilimine compound is affected by the amount of reaction by-products produced. For instance, 5-[1-(methylthio)ethyl]-2-trifluoromethylpyridine (the sulfide compound) is oxidized to N-cyano-S-methyl-S-[1-(6-trifluoromethyl-3-pyridinyl)ethyl]sulfilimine (the sulfilimine compound) in the presence of sodium hypochlorite and cyanamide. A by-product of the oxidation reaction is 5-[1-(methylsulfinyl)ethyl]-2-trifluoromethylpyridine (the sulfoxide compound), which may be produced at 10% or greater. It would be desirable to have a process for producing the sulfilimine compound at higher yields, such as by decreasing the amount of sulfoxide compound produced.

BRIEF SUMMARY

An embodiment of the present disclosure includes a method of producing a sulfilimine compound that comprises combining a sulfide compound, cyanamide, a hypochlorite compound, and a base. The sulfide compound is oxidized to form a sulfilimine compound.

Another embodiment of the present disclosure includes a method of producing a sulfilimine compound that comprises combining a 5-[1-(alkylthio)alkyl]-2-trifluoromethylpyridine compound, cyanamide, a hypochlorite compound, and a base to form a sulfilimine compound.

Yet another embodiment of the present disclosure includes a method of producing N-cyano-S-methyl-S-[1-(6-trifluoromethyl-3-pyridinyl)ethyl]sulfilimine that comprises providing a feed stream comprising 5-[1-(methylthio)ethyl]-2-trifluoromethylpyridine and acidic impurities. An aqueous cyanamide solution, an aqueous sodium hypochlorite solution, an aqueous sodium hydroxide solution, and acetonitrile are combined with the feed stream. An organic phase comprising N-cyano-S-methyl-S-[1-(6-trifluoromethyl-3-pyridinyl)ethyl]sulfilimine is separated from an aqueous phase.

DETAILED DESCRIPTION

A method of producing a sulfilimine compound from a sulfide compound is described. The method provides an increased yield of the sulfilimine compound and a decreased yield of reaction by-products. The sulfilimine compound is synthesized by combining a sulfide compound, cyanamide, a hypochlorite compound, a base, and, optionally, a buffer. The sulfide compound may be provided in a sulfide feed stream, which is produced by a previous reaction in the overall process of producing the sulfilimine compound. By way of example, the sulfide feed stream may be a feed stream from a reaction to produce the sulfide compound from a substituted enamine compound. However, the sulfide feed stream may be produced from other types of reactions. The sulfide feed stream may be used directly from the previous reaction, or may be subjected to conventional solvent exchange process, conventional solvent concentration process, or conventional purification techniques before use in the reaction to produce the sulfilimine compound. The sulfide compound in the sulfide feed stream may be at least 90% pure. The sulfide feed stream may also include acidic impurities, such as by-products from the previous reaction. Acidic impurities may also be present in the cyanamide.

The cyanamide solution and sulfide compound may be combined in the organic solvent, the base and buffer, if present, added thereto, followed by addition of the hypochlorite compound. A small amount of aqueous sodium bisulfite solution may be added to the mixture to react with any excess hypochlorite compound. The presence of excess hypochlorite compound may be determined by testing with starch-iodide paper. After a sufficient amount of time has passed for the reagents to react, an aqueous phase may be separated from an organic phase, which contains the sulfilimine compound. The organic phase including the sulfilimine compound may be used directly in a subsequent oxidation to produce an insecticidal sulfoximine compound by conventional techniques or the sulfilimine compound may be isolated and purified by conventional techniques, which are not described in detail herein.

As used herein, the terms "alkyl," "alkenyl," and "alkynyl," as well as derivative terms such as "alkoxy," "acyl," "alkylthio," "arylalkyl," "heteroarylalkyl," and "alkylsulfonyl," include within their scope straight chain, branched chain, or cyclic moieties. Thus, the term "alkyl" may include, but is not limited to, methyl, ethyl, 1-methylethyl, propyl, 1,1-dimethylethyl, or cyclopropyl. Unless specifically stated otherwise, each may be unsubstituted or substituted with one or more substituents including, but not limited to, a halogen, hydroxy, an alkoxy, an alkylthio, a $C_1$-$C_6$ acyl, a formyl, cyano, an aryloxy, or an aryl group, provided that the substituents are sterically compatible and the rules of chemical bonding and strain energy are satisfied. The terms "haloalkyl" and "haloalkenyl" include alkyl and alkenyl groups substituted with from one to the maximum possible number of halogen atoms, all combinations of halogens included. The terms "halogen" or "halo" includes fluorine, chlorine, bromine, iodine, or combinations thereof. In one embodiment, the halogen is fluorine. The terms "alkenyl" and "alkynyl" are intended to include one or more unsaturated bonds.

The term "aryl" refers to a phenyl, indanyl, or naphthyl group. The term "heteroaryl" refers to a 5- or 6-membered aromatic ring containing one or more heteroatoms, such as nitrogen, oxygen, or sulfur. These heteroaromatic rings may be fused to other aromatic systems. The aryl or heteroaryl groups may be unsubstituted, or substituted with one or more substituents selected from a halogen, hydroxy, nitro, cyano, an aryloxy, formyl, a $C_1$-$C_6$ alkyl, a $C_2$-$C_6$ alkenyl, a $C_2$-$C_6$ alkynyl, a $C_1$-$C_6$ alkoxy, a halogenated $C_1$-$C_6$ alkyl, a halogenated $C_1$-$C_6$ alkoxy, a $C_1$-$C_6$ acyl, a $C_1$-$C_6$ alkylthio, a $C_1$-$C_6$ alkylsulfinyl, a $C_1$-$C_6$ alkylsulfonyl, an aryl, a $C_1$-$C_6$OC(O)alkyl, a $C_1$-$C_6$ NHC(O)alkyl, C(O)OH, a $C_1$-$C_6$C(O)Oalkyl, C(O)NH$_2$, a $C_1$-$C_6$C(O)NHalkyl, or a $C_1$-$C_6$C(O)N(alkyl)$_2$, provided that the substituents are sterically compatible and the rules of chemical bonding and strain energy are satisfied.

The sulfilimine compound produced by the oxidation reaction may be a substituted sulfilimine compound, such as one of the compounds described in U.S. Pat. No. 7,868,027, the disclosure of which is incorporated by reference herein in its entirety. By way of example, the sulfilimine compound may have the following chemical structure:

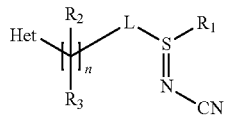

where "Het" is a heteroaryl group and is selected from one of the following chemical structures:

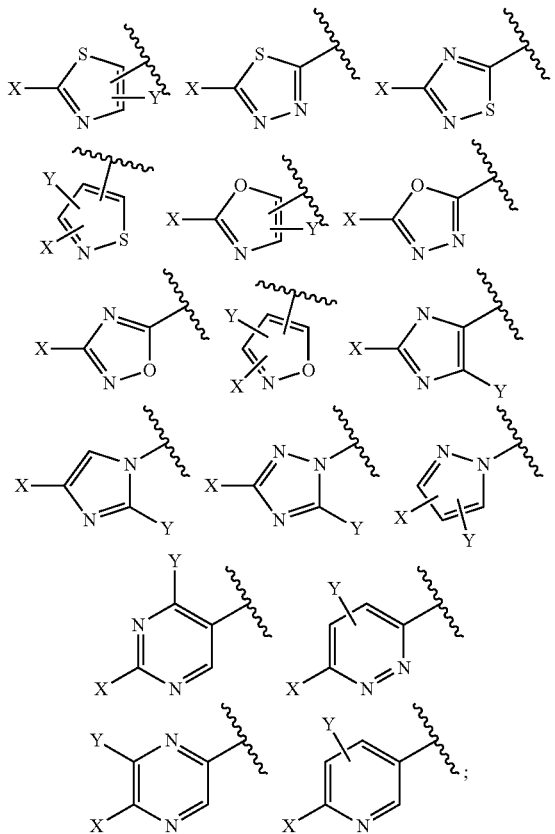

X is a halogen, a $C_1$-$C_4$ alkyl, a $C_1$-$C_4$ haloalkyl, a $C_2$-$C_4$ alkenyl, a $C_2$-$C_4$ alkynyl, a $C_2$-$C_4$ haloalkenyl, a $C_1$-$C_4$ alkoxy, a $C_1$-$C_4$ haloalkoxy, CN, NO$_2$, SO$_m$R$_6$ where m is an integer from 0-2, COOR$_4$, or CONR$_4$R$_5$;

Y is hydrogen, a halogen, a $C_1$-$C_4$ alkyl, a $C_1$-$C_4$ haloalkyl, a $C_2$-$C_4$ alkenyl, a $C_2$-$C_4$ alkynyl, a $C_2$-$C_4$ haloalkenyl, a $C_1$-$C_4$ alkoxy, a $C_1$-$C_4$ haloalkoxy, CN, NO$_2$, SO$_m$R$_1$ where m is an integer from 0-2, COOR$_4$, CONR$_4$R$_5$, aryl, or heteroaryl;

n is an integer from 0-3;

L is either a single bond, —CH(CH$_2$)$_p$— where R$_1$, S, and L taken together are a 4-, 5-, or 6-membered ring, and p is an integer from 1-3, —CH(CH$_2$OCH$_2$)— where R$_1$, S, and L taken together are a 6-membered ring, or —CH— where L, R$_2$, and the common carbon to which they connect taken together are a 4-, 5-, or 6-membered ring with up to, but no more than, 1 heteroatom;

R$_1$ is a $C_1$-$C_4$ alkyl, a $C_1$-$C_4$ haloalkyl, a $C_3$-$C_6$ alkenyl, a $C_3$-$C_6$ alkynyl, a $C_3$-$C_6$ haloalkenyl, an arylalkyl, a heteroarylalkyl, or —CH$_2$— in cases where R$_1$, S, and L taken together are a 4-, 5-, or 6-membered ring;

R$_2$ and R$_3$ independently are hydrogen, halogen, $C_1$-$C_4$ alkyl, a $C_1$-$C_4$ haloalkyl, a $C_2$-$C_4$ alkenyl, a $C_2$-$C_4$ alkynyl, a $C_2$-$C_4$ haloalkenyl, a $C_1$-$C_4$ alkoxy, a $C_1$-$C_4$ haloalkoxy, CN, SO$_m$R$_6$ where m is an integer from 0-2, COOR$_4$, CONR$_4$R$_5$, an arylalkyl, a heteroarylalkyl, or R$_2$ and R$_3$ and the common carbon to which they attach form a 3-6 membered ring;

R$_4$ and R$_5$ independently are hydrogen, a $C_1$-$C_4$ alkyl, a $C_1$-$C_4$ haloalkyl, a $C_3$-$C_6$ alkenyl, a $C_3$-$C_6$ alkynyl, a $C_3$-$C_6$ haloalkenyl, an aryl, a heteroaryl, an arylalkyl, or a heteroarylalkyl; and R$_6$ represents a $C_1$-$C_4$ alkyl, a $C_1$-$C_4$ haloalkyl, a $C_3$-$C_6$ alkenyl, a $C_3$-$C_6$ alkynyl, a $C_3$-$C_6$ haloalkenyl, an arylalkyl, or a heteroarylalkyl.

In one embodiment, the sulfilimine compound is N-cyano-S-methyl-S-[1-(6-trifluoromethyl-3-pyridinyl)ethyl]sulfilimine.

The sulfilimine compound may be produced by reacting a corresponding sulfide compound with the hypochlorite compound, cyanamide, base, and buffer, if present. The sulfide compound may have the following chemical structure:

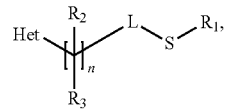

where Het, R$_1$, R$_2$, R$_3$, and L are defined as previously discussed, and n is an integer from 0-3. In one embodiment, the sulfide compound is a 2-trifluoromethyl-5-(1-substituted) alkylthiopyridine compound having the following chemical structure:

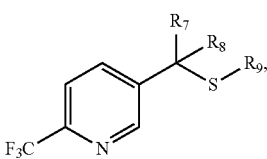

where R$_7$ and R$_8$ are independently H, $C_1$-$C_4$ alkyl, or either of R$_7$ or R$_8$ taken together with R$_9$ is a 4- to 6-membered saturated ring or R$_7$ taken together with R$_8$ is a 3- to 6-membered saturated ring optionally substituted with an O or a N atom, and R$_9$ is a $C_1$-$C_4$ alkyl or R$_9$ taken together with either of R$_7$ or R$_8$ is a 4- to 6-membered saturated ring. In one embodiment, the 2-trifluoromethyl-5-(1-substituted)alkylpyridine compound is 5-[1-(methylthio)ethyl]-2-trifluoromethylpyridine.

In one embodiment, the 2-trifluoromethyl-5-(1-substituted)alkylthiopyridine compound is 5-[1-(methylthio)ethyl]-2-trifluoromethylpyridine and the sulfilimine compound produced therefrom is N-cyano-S-methyl-S-[1-(6-trifluoromethyl-3-pyridinyl)ethyl]sulfilimine with 5-[1-(methylsulfinyl)-ethyl]-2-trifluoromethylpyridine potentially produced as a sulfoxide by-product of the oxidation reaction. However, the addition of the base and buffer, if present, may reduce the amount of sulfoxide by-product produced by the reaction.

The 2-trifluoromethyl-5-(1-substituted)alkylpyridine compound may be oxidized to the corresponding sulfilimine compound, which may subsequently be oxidized to produce a sulfoximine compound having insecticidal activity. While the examples herein describe the production of N-cyano-S-methyl-S-[1-(6-trifluoromethyl-3-pyridinyl)ethyl]sulfilimine from 5-[1-(methylthio)ethyl]-2-trifluoromethylpyridine, a similar method may be used to form other sulfilimine compounds from their corresponding sulfide compounds.

The 2-trifluoromethyl-5-(1-substituted)alkylthiopyridine compound may be oxidized to the corresponding sulfilimine compound by reacting the 2-trifluoromethyl-5-(1-substituted)-alkylthiopyridine compound, cyanamide, hypochlorite compound, base, and buffer, if present. The oxidation reaction may be conducted in a suitable organic solvent that is substantially inert to the strong oxidizing conditions of the reaction and that facilitates partitioning of the resulting sulfilimine compound. By way of example, the organic solvent may be an aliphatic hydrocarbon, such as petroleum ether; a halogenated aliphatic or halogenated aromatic hydrocarbon, such as dichloromethane, chloroform, 1,2-dichloroethane, or dichlorobenzene; or an aliphatic or aromatic nitrile, such as acetonitrile (ACN) or benzonitrile. In one embodiment, the organic solvent is acetonitrile. The oxidation reaction may also be conducted in a biphasic solvent system that includes a mixture of the organic solvent, such as a halogenated hydrocarbon, and water. The oxidation reaction may be conducted at a temperature within a range of from about −40° C. to about 30° C., such as from about −10° C. to about 10° C., or from about −5° C. to about 0° C. The preferred method is to slowly add the hypochlorite compound to a mixture of the 2-trifluoromethyl-5-(1-substituted)alkylthiopyridine compound, solvent, cyanamide, base, and buffer, if present. The reagents, once completely mixed, may be stirred for from approximately 15 minutes to approximately 2 hours, such as for approximately 30 minutes, to provide sufficient time for the oxidation reaction to occur.

The 2-trifluoromethyl-5-(1-substituted)alkylthiopyridine compound, cyanamide, base, and buffer (if present) may be combined in any order, with the hypochlorite solution being slowly added last to help control the heat of reaction. By way of example, the base may be added to the sulfide feed stream containing the 2-trifluoromethyl-5-(1-substituted)alkylthiopyridine compound, followed by addition of the remaining reagents, with the hypochlorite compound added last. Other addition orders are possible but precautions need to be taken to deal with unstable intermediates. The base may neutralize the acidic impurities in the sulfide feed stream or in the cyanamide, enabling production of a higher yield of the sulfilimine compound.

The sulfide feed stream including the 2-trifluoromethyl-5-(1-substituted)alkyl-thiopyridine compound may be contacted with a solution of the base, followed by addition of the cyanamide, hypochlorite compound, and buffer (if present).

The sulfide feed stream may include the 2-trifluoromethyl-5-(1-substituted)alkylthiopyridine compound and acidic impurities, which may include, but are not limited to, acetic acid, hydrochloric acid, or other acidic by-products from a previous reaction. The sulfide feed stream may include the 2-trifluoromethyl-5-(1-substituted)alkylthiopyridine compound and from about $1 \times 10^{-5}$ moles of acidic impurities to about $1 \times 10^{-4}$ moles of acidic impurities per gram. The cyanamide is buffered to a pH of 4 to 5 to improve its storage stability, thus the cyanamide will add acidity to the system.

The base may be a suitable base of sufficient strength to neutralize the acidic impurities in the sulfide feed stream or the cyanamide. The base may be added to the sulfide feed stream. The base may be an alkali metal hydroxide, an alkali metal carbonate, or combinations thereof. By way of example, the base may be lithium hydroxide, sodium hydroxide (NaOH), potassium hydroxide, lithium carbonate, sodium carbonate, potassium carbonate, trisodium and tripotassium phosphates, or combinations thereof. In one embodiment, the base is sodium hydroxide. In another embodiment, the base is sodium carbonate. The base used in the oxidation reaction may be a solid or an aqueous solution. The base may be combined with the additional reagents to neutralize the acidic impurities in the sulfide feed stream or the cyanamide. The moles of base should meet or exceed the moles of acid.

The cyanamide used in the oxidation reaction may be a solid or an aqueous solution that includes from approximately 40% by weight to approximately 60% by weight of cyanamide. In one embodiment, the cyanamide is a solution including 50% by weight of cyanamide in water. In a particular embodiment, the oxidation reaction may utilize a stoichiometric amount of cyanamide relative to the 2-trifluoromethyl-5-(1-substituted)alkylthiopyridine compound, or from about 1.0 molar equivalents to about up to 1.6 molar equivalents of the cyanamide relative to the 2-trifluoromethyl-5-(1-substituted)alkylthiopyridine compound. To ensure complete conversion of the 2-trifluoromethyl-5-(1-substituted)alkylthiopyridine compound, an excess of the cyanamide (relative to the 2-trifluoromethyl-5-(1-substituted)alkylthiopyridine compound) may be used.

The hypochlorite compound used in the oxidation reaction may be a hypochlorite solution. The hypochlorite compound may be a metallic salt of hypochlorous acid. The metallic salt may be a Group I alkali metal salt or a Group II alkaline earth metal salt of hypochlorous acid, such as sodium hypochlorite or calcium hypochlorite. The hypochlorite solution may include the metallic salt of hypochlorous acid and water. The hypochlorite solution may include from about 2% by weight to about 20% by weight of the metallic salt of hypochlorous acid, such as from about 12.5% by weight to about 17% by weight. The hypochlorite solution may be commercially available, such as from Sigma-Aldrich Co. or other chemical supply company. Higher concentrations of chlorine in the hypochlorite solution may be achieved by adding chlorine to the hypochlorite solution to provide a solution containing up to approximately 20% of the hypochlorite compound. In particular embodiments, a stoichiometric amount of the hypochlorite compound may be utilized relative to the 2-trifluoromethyl-5-(1-substituted)alkylthiopyridine compound or from about 1.0 to about 1.2 molar equivalents of the hypochlorite compound may be used relative to the 2-trifluoromethyl-5-(1-substituted)alkylthiopyridine compound. To ensure complete conversion of the 2-trifluoromethyl-5-(1-substituted)alkylthiopyridine compound, an excess of the hypochlorite (relative to the 2-trifluoromethyl-5-(1-substituted)alkylthiopyridine compound) may be used. In one embodiment, the hypochlorite solution includes 13% by weight of sodium hypochlorite. In another embodiment, the hypochlorite solution includes 15% by weight of sodium hypochlorite. In yet another embodiment, the hypochlorite solution includes 17% by weight of sodium hypochlorite.

The buffer may be a phosphate buffer, such as sodium dihydrogen phosphate. The buffer may be added to the sulfide feed stream or the cyanamide. The buffer may be present at from about 1 mole % to about 5 mole % relative to the 2-trifluoromethyl-5-(1-substituted)alkylthiopyridine compound. After addition of the buffer, a known amount of the base may be added such that all of the phosphate buffer is in the form of disodium hydrogen phosphate or tri-sodium phosphate.

After a sufficient amount of time has passed for the reagents to react, an aqueous phase may be separated from an organic phase, which contains the corresponding sulfilimine compound (N-cyano-S-methyl-S-[1-(6-trifluoromethyl-3-pyridinyl)ethyl]sulfilimine). The organic phase including the corresponding sulfilimine compound may be used directly in a subsequent reaction to produce an insecticidal sulfoximine compound by conventional techniques, or the sulfilimine compound may be isolated and purified by conventional techniques, which are not described in detail herein. The use of the base and buffer, if present, in the oxidation reaction may reduce the formation of 5-[1-(methylsulfinyl)-ethyl]-2-trifluoromethylpyridine as a by-product of the oxidation reaction, resulting in an increased yield of the N-cyano-S-methyl-S-[1-(6-trifluoromethyl-3-pyridinyl)ethyl]sulfilimine.

In an additional embodiment, the pH of a mixture including the 2-trifluoromethyl-5-(1-substituted)alkylthiopyridine compound, cyanamide, and hypochlorite compound may be determined, and then a desired amount of the base added to neutralize the mixture. By way of example, a sufficient amount of the base may be added to the mixture to neutralize the acidic impurities therein. The mixture may be titrated with the solution of base to neutralize the acidic impurities. By first quantitating the acidity of the mixture, the mixture may be neutralized without adding excess base, which can result in incomplete conversion of the 2-trifluoromethyl-5-(1-substituted)alkylthiopyridine compound.

In another embodiment, an excess of the buffer may be added to the mixture including the 2-trifluoromethyl-5-(1-substituted)alkylthiopyridine compound and cyanamide followed by addition of the base. By adding an excess amount of the base, neutralization of the acidic impurities may be ensured without having to first measure the acidity of the mixture.

The following examples serve to explain embodiments of the present disclosure in more detail. These examples are not to be construed as being exhaustive or exclusive as to the scope of this invention.

EXAMPLES

Example 1

Preparation of N-cyano-S-methyl-S-[1-(6-trifluoromethyl-3-pyridinyl)ethyl]sulfilimine: 5-[1-(methylthio)ethyl]-2-trifluoromethylpyridine pre-treatment The starting sulfide compound was pre-treated with base to remove acidic compounds. 5-[1-methylthio)ethyl]-2-trifluoromethylpyridine was dissolved in hexane and washed with an equal volume of 1% aqueous sodium hydroxide (NaOH). The resulting organic phase was evaporated and the remaining oil used as feed for the sulfilimine reaction. The above treated 5-[1-methylthio)ethyl]-2-trifluoromethylpyridine, 10.6 g (about 0.045 moles) was mixed with 39.2 g of acetonitrile and 5.06 g (0.059 moles) of 50% aqueous cyanamide in a 250 ml flask equipped with electric stirrer (half moon agitator), thermowell, nitrogen pad, and addition funnel. Using a bath the flask was cooled to −7° C. A 6.14% solution of sodium hypochlorite (68.1 g, 0.056 moles) was slowly added over 88 minutes, keeping the temperature at −7° C. After a 35 minute post reaction period the excess oxidizing agents were quenched with sodium bisulfite to give a negative test to starch-iodide paper. The mixture was warmed to room temperature and phase separated. The total accountability as the sulfilimine in the two phases was 90.1% and the total accountability as the sulfoxide was 10.1%. Without first treating the 5-[1-methylthio)ethyl]-2-trifluoromethylpyridine with the hexane and base, the accountibilities of the sulfilimine and sulfoxide respectively were 85.6% and 13.7%.

Example 2

Preparation of N-cyano-S-methyl-S-[1-(6-trifluoromethyl-3-pyridinyl)ethyl]sulfilimine: Sodium Dihydrogen Phosphate and Base Addition An acid (sodium dihydrogen phosphate) was added to the mixture to simulate the effects of low levels of acid in the sulfide feed stream. Cyanamide (1.4 molar equivalents relative to the 5-[1-(methylthio)ethyl]-2-trifluoromethylpyridine), water, and 2 mole % of the sodium dihydrogen phosphate were mixed until homogeneous. ACN and the sulfide feed stream (5-[1-(methylthio)ethyl]-2-trifluoromethylpyridine (94% purity)) were then added. The mixture turned cloudy, indicating precipitation of some of the sodium dihydrogen phosphate. The mixture was cooled to the desired reaction temperature and 1.25 molar equivalents of 13% sodium hypochlorite was slowly added. Additional oxidation reactions were conducted, adding sodium carbonate ($Na_2CO_3$) or NaOH along with the sodium dihydrogen phosphate. All oxidation reactions used 1.4 molar equivalents of cyanamide and 1.25 molar equivalents of 13% sodium hypochlorite relative to the 5-[1-(methylthio)ethyl]-2-trifluoromethylpyridine. All runs resulted in 99+% conversion of the 5-[1-(methylthio)ethyl]-2-trifluoromethylpyridine to reaction products. The results are summarized in Table 1.

TABLE 1

| Run Number | $NaH_2PO_4$ (mole percent) | Base | Sulfilimine Compound (% Yield) | Sulfoxide Compound (% Yield) |
|---|---|---|---|---|
| 1 | none | none | 92.8 | 5.91 |
| 2 | 2 | none | 87.3 | 10.29 |
| 3 | 2 | $Na_2CO_3$ (2 moles per mole of $NaH_2PO_4$) | 89.4 | 9.87 |
| 4 | 2 | NaOH (2 moles per mole of $NaH_2PO_4$) | 93.5 | 5.63 |

The addition of the sodium dihydrogen phosphate to the mixture almost doubled the amount of sulfoxide compound (5-[1-(methylsulfinyl)ethyl]-2-trifluoromethylpyridine) produced, thus reducing the yield of sulfilimine compound (N-cyano-S-methyl-S-[1-(6-trifluoromethyl-3-pyridinyl) ethyl]sulfilimine) by around 5%. The addition of the sodium carbonate had minimal effect. The addition of the sodium hydroxide increased the yield of sulfilimine compound to approximately the same as the baseline or even slightly better. The results in Table 1 indicate that the addition of NaOH to the sulfide feed stream contaminated with acids increased the yield of sulfilimine compound.

Example 3

Preparation of N-cyano-S-methyl-S-[1-(6-trifluoromethyl-3-pyridinyl)ethyl]sulfilimine: Base Addition A sulfide feed stream known to include acidic impurities was titrated with dilute NaOH and found to contain about $3.2 \times 10^{-5}$ moles of acid/gram. The cyanamide was titrated with dilute NaOH and found to contain about $2.01 \times 10^{-5}$ moles of acid/gram. Thus, for the oxidation reaction of 5-[1-(methylthio)ethyl]-2-trifluoromethylpyridine with cyanamide and sodium hypochlorite (13%) conducted on a 0.047 mole scale, the total moles of acid in the mixture was 0.00041 moles. The effect of adding NaOH to the mixture to neutralize the acidity in the sulfide feed stream and the cyanamide was determined. The NaOH was added as a 25% aqueous solution and stirred for about 5 minutes before adding the sodium hypochlorite. The results are summarized in Table 2.

TABLE 2

| Run Number | Moles NaOH | Sulfilimine Compound (% Yield) | Sulfoxide compound (% Yield) |
|---|---|---|---|
| 1 | None | 89.3 | 7.85 |
| 2 | 0.00130 | 91.2 | 5.82 |
| 3 | 0.00064 | 91.5 | 5.81 |

Table 2 indicates that adding the NaOH to the mixture increased the yield of the sulfilimine compound and decreased the yield of the sulfoxide compound.

Example 4

Preparation of N-cyano-S-methyl-S-[1-(6-trifluoromethyl-3-pyridinyl)ethyl]sulfilimine: Buffer Addition The effect of adding a phosphate buffer to the sulfide feed stream on the yields of sulfilimine compound and sulfoxide compound was investigated in accordance with the procedures disclosed in Example 1 using 12% aqueous sodium hypochlorite. The phosphate buffer was trisodium phosphate or sodium dihydrogen phosphate, with sufficient sodium hydroxide used to generate the trisodium salt. The results are summarized in Table 3.

TABLE 3

| Run Number | Phosphate (mole %) | Sulfilimine Compound (% Yield) | Sulfoxide Compound (% Yield) |
|---|---|---|---|
| 1 | 3 | 92.0 | 5.43 |
| 2 | 2 | 90.8 | 5.64 |
| 3 | 2 | 89.3 | 5.68 |
| 4 | 2 | 88.9 | 5.72 |
| 5 | 2 | 90.0 | 5.63 |
| 6 | 2 | 90.1 | 5.84 |
| Average | | 90.2 | 5.66 |
| 7 | None | 89.2 | 6.32 |
| 8 | None | 89.5 | 6.50 |
| Average | | 89.35 | 6.41 |

The addition of the phosphate buffer to the sulfide feed stream resulted in an increased yield of sulfilimine compound, as evidenced in Table 3 by the difference in average sulfimine compound yield between the runs including the phosphate buffer compared to those lacking the phosphate buffer.

The effect on yields of the sulfilimine compound and sulfoxide compound by varying the amount of phosphate buffer used was also investigated. The phosphate buffer was added in such a way as to produce trisodium phosphate. The results are summarized in Table 4.

TABLE 4

| Run Number | Phosphate Buffer (mole %) | Sulfilimine Compound (% Yield) | Sulfoxide Compound (% Yield) |
|---|---|---|---|
| 1 | None | 89.35 | 6.41 |
| 2 | 1 | 89.1 | 5.66 |
| 3 | 2 | 89.8 | 5.70 |
| 4 | 3 | 92.0 | 5.43 |
| 5 | 5 | 89.7 | 6.01 |

A positive effect of adding the phosphate buffer to the sulfide feed stream was seen in the range of evaluated 1-5 mole % of phosphate buffer relative to the sulfide compound.

While the invention may be susceptible to various modifications and alternative forms, specific embodiments have been described by way of example in detail herein. However, it should be understood that the invention is not intended to be limited to the particular forms disclosed. Rather, the invention is to cover all modifications, equivalents, and alternatives falling within the scope of the invention as defined by the following appended claims and their legal equivalents.

What is claimed is:

1. A method of producing a sulfilimine compound, comprising:
   reacting 2-trifluoromethyl-5-(1-substituted)alkylthiopyridine compound with cyanamide, hypochlorite compound, and base to form a sulfilimine compound,
   wherein the base is selected from the group consisting of alkali metal hydroxide, alkali metal carbonate, and combinations thereof,
   wherein the 2-trifluoromethyl-5-(1-substituted)alkylthiopyridine compound has the following formula:

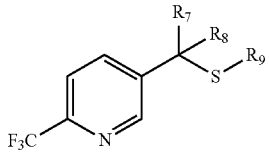

wherein
   each of $R_7$ and $R_8$ is independently selected from the group consisting of hydrogen and $C_1$-$C_4$ alkyl; or $R_7$ taken together with $R_8$ is a 3- to 6-membered saturated ring; or $R_7$ taken together with $R_8$ is a 4- to 6-membered saturated ring containing at least one of O or N atom, and
   $R_9$ is a $C_1$-$C_4$ alkyl; or $R_9$ taken together with either of $R_7$ or $R_8$ is a 4- to 6-membered saturated ring.

2. The method of claim 1, wherein reacting 2-trifluoromethyl-5-(1-substituted)alkylthiopyridine compound with cyanamide, hypochlorite compound, and base comprises oxidizing the 2-trifluoromethyl-5-(1-substituted)alkylthiopyridine compound with a hypochlorite compound solution comprising from 2% by weight to 20% by weight of a metallic salt of hypochlorous acid, in the presence of the cyanamide and the base.

3. The method of claim 1, wherein reacting 2-trifluoromethyl-5-(1-substituted)alkylthiopyridine compound with cyanamide, hypochlorite compound, and base comprises combining the 2-trifluoromethyl-5-(1-substituted)alkylthiopyridine compound with the cyanamide and the alkaline metal hydroxide to provide a mixture, and then adding the hypochlorite compound to the mixture.

4. The method of claim 1, wherein reacting a reacting 2-trifluoromethyl-5-(1-substituted)alkylthiopyridine compound with cyanimide, hypochlorite compound, and base comprises reacting the 2-trifluoromethyl-5-(1-substituted)alkylthiopyridine compound with the cyanamide, the hypochlorite compound, and sodium hydroxide.

5. The method of claim 1, wherein reacting 2-trifluoromethyl-5-(1-substituted)alkylthiopyridine compound with cyanamide, hypochlorite compound, and base comprises reacting 5-[1-(methylthio)ethyl]-2-trifluoromethylpyridine with the cyanamide, sodium hypochlorite, and sodium hydroxide to form the sulfilimine compound.

6. The method of claim 3, further comprising adding a phosphate buffer to the mixture.

7. A method of producing N-cyano-S-methyl-S-[1-(6-trifluoromethyl-3-pyridinypethyl] sulfilimine, comprising:
combining 5-[1-(methylthio)ethyl]-2-trifluoromethylpyridine with cyanamide and sodium hydroxide to provide a mixture; and
adding sodium hypochlorite to the mixture to oxidize the 5-[1-(methylthio)ethyl]-2-trifluoromethylpyridine to N-cyano-S-methyl-S- [1 -(6-trifluoromethyl-3 -pyridinyl)ethyl]sulfilimine.

8. The method of claim 7, wherein the 5-[1-(methylthio) ethyl]-2-trifluoromethylpyridine comprises from $1\times10^{-5}$ moles of acidic impurities to $1\times10^{-4}$ moles of acidic impurities per gram of the mixture.

9. The method of claim 7, wherein adding sodium hypochlorite to the mixture comprises adding an aqueous sodium hypochlorite solution comprising from 12.5% by weight to 17% by weight of sodium hypochlorite to the mixture.

10. The method of claim 7, wherein adding sodium hypochlorite to the mixture comprises adding an aqueous sodium hypochlorite solution comprising from 12.5% by weight to 20% by weight of sodium hypochlorite to the mixture.

11. The method of claim 7, wherein
combining 5- [1-(methylthio)ethyl]-2-trifluoromethylpyridine with cyanamide and sodium hydroxide to provide a mixture comprises combining the 5-[1-(methylthio) ethyl]-2-trifluoromethylpyridine with from 1.0 molar equivalents to 1.6 molar equivalents of the cyanamide relative to the 5[1-(methylthio)ethyl]-2-trifluoromethylpyridine, and the sodium hydroxide to provide the mixture; and
adding sodium hypochlorite to the mixture comprises adding from 1.0 to 1.2 molar equivalents of the sodium hypochlorite relative to the 5-[1-(methylthio)ethyl]-2-trifluoromethylpyridine to the mixture.

12. The method of claim 11, wherein molar ratio of cyanamide to sodium hypochlorite is 1.2.

13. A method of producing a sulfilimine compound, comprising oxidizing 2-trifluoromethyl-5-(1-substituted)alkylthiopyridine compound with sodium hypochlorite compound in the presence of sodium hydroxide (NaOH) base and cyanamide at a temperature from -40° C. to 30° C. to form a sulfilimine compound, wherein the 2-trifluoromethyl-5-(1-substituted)alkylthiopyridine compound has the following formula:

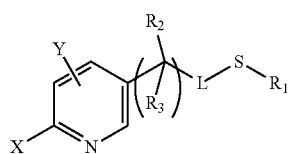

wherein
X is a moiety selected from the group consisting of a halogen, a $C_1$-$C_4$ alkyl, a $C_1$-$C_4$ haloalkyl, a $C_2$-$C_4$ alkenyl, a $C_2$-$C_4$ alkynyl, a $C_2$-$C_4$ haloalkenyl, a $C_1$-$C_4$ alkoxy, a $C_1$-$C_4$ haloalkoxy, CN, $NO_2$, $SO_mR_6$ where m is an integer from 0-2, $COOR_4$, and $CONR_4R_5$;
Y is a moiety selected from the group consisting of hydrogen, a halogen, a $C_1$-$C_4$ alkyl, a $C_1$-$C_4$ haloalkyl, a $C_2$-$C_4$ alkenyl, a $C_2$-$C_4$ alkynyl, a $C_2$-$C_4$ haloalkenyl, a $C_1$-$C_4$ alkoxy, a $C_1$-$C_4$ haloalkoxy, CN, $NO_2$, $SO_mR_1$ where m is an integer from 0-2, $COOR_4$, $CONR_4R5$, aryl. and heteroaryl;
n is an integer from 0-3;
L is either a single bond; —CH(CH$_2$)$_p$— where $R_1$, S, and L taken together are a 4-, 5-, or 6-membered ring and p is an integer from 1-3; —CH(CH$_2$OCH$_2$)— where $R_1$, S, and L taken together are a 6-membered ring; or —CH— where L, $R_2$, and the common carbon to which they connect taken together are a 5-membered or 6-membered ring with up to, but no more than, 1 heteroatom;
$R_1$ is a moiety selected from the group consisting of a $C_1$-$C_4$ alkyl, a $C_1$-$C_4$ haloalkyl, a $C_3$-$C_6$ alkenyl, a $C_3$-$C_6$ alkynyl, a $C_3$-$C_6$ haloalkenyl, an arylalkyl, a heteroarylalkyl, or —CH$_2$— in cases where $R_1$, S, and L taken together are a 4-, 5-, or 6-membered ring;
each of $R_2$ and $R_3$ is independently selected from the group consisting of hydrogen, halogen, $C_1$-$C_4$ alkyl, a $C_1$-$C_4$ haloalkyl, a $C_2$-$C_4$ alkenyl, a $C_2$-$C_4$ alkynyl, a $C_2$-$C_4$ haloalkenyl, a $C_1$-$C_4$ alkoxy, a $C_1$-$C_4$ haloalkoxy, CN, $SO_mR_6$ where m is an integer from 0-2, $COOR_4$, $CONR_4R_5$, an arylalkyl, a heteroarylalkyl, or $R_2$ and $R_3$ and the common carbon to which they attach form a 3-6 membered ring;
each of $R_4$ and $R_5$ is independently selected from the group consisting of hydrogen, a $C_1$-$C_4$ alkyl, a $C_1$-$C_4$ haloalkyl, a $C_3$-$C_6$ alkenyl, a $C_3$-$C_6$ alkynyl, a $C_3$-$C_6$ haloalkenyl, an aryl, a heteroaryl, an arylalkyl, or a heteroarylalkyl; and
$R_6$ is a moiety selected from the group consisting of a $C_1$-$C_4$ alkyl, a $C_1$-$C_4$ haloalkyl, a $C_3$-$C_6$ alkenyl, a $C_3$-$C_6$ alkynyl, a $C_3$-$C_6$ haloalkenyl, an arylalkyl, and a heteroarylalkyl.

* * * * *